US010603021B2

(12) United States Patent
Rogers et al.

(10) Patent No.: US 10,603,021 B2
(45) Date of Patent: Mar. 31, 2020

(54) ENDO-CAMERAL CLOSURE DEVICE

(71) Applicant: The United States of America, as represented by the Secretary, Department of Health and Human Services, Bethesda, MD (US)

(72) Inventors: Toby Rogers, Washington, DC (US); Merdim Sonmez, Chevy Chase, MD (US); Ozgur Kocaturk, Rockville, MD (US); Robert J. Lederman, Chevy Chase, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 126 days.

(21) Appl. No.: 15/761,923

(22) PCT Filed: Sep. 30, 2016

(86) PCT No.: PCT/US2016/054961
§ 371 (c)(1),
(2) Date: Mar. 21, 2018

(87) PCT Pub. No.: WO2017/059339
PCT Pub. Date: Apr. 6, 2017

(65) Prior Publication Data
US 2018/0280006 A1 Oct. 4, 2018

Related U.S. Application Data

(60) Provisional application No. 62/236,734, filed on Oct. 2, 2015.

(51) Int. Cl.
*A61B 17/00* (2006.01)

(52) U.S. Cl.
CPC ............. *A61B 17/0057* (2013.01); *A61B 2017/00575* (2013.01); *A61B 2017/00592* (2013.01);
(Continued)

(58) Field of Classification Search
CPC ...... A61B 17/0057; A61B 2017/00867; A61B 2017/00575; A61B 2017/00592;
(Continued)

(56) References Cited

U.S. PATENT DOCUMENTS 5,976,174 A 11/1999 Ruiz
7,665,466 B2 2/2010 Figulla et al.
(Continued)

FOREIGN PATENT DOCUMENTS

WO    WO 02071977    9/2002

OTHER PUBLICATIONS

European Extended Search Report for App. No. 16852768.7, dated Apr. 11, 2019, 9 pages.
(Continued)

*Primary Examiner* — Wade Miles
*Assistant Examiner* — Mikail A Mannan
(74) *Attorney, Agent, or Firm* — Klarquist Sparkman, LLP

(57) ABSTRACT

Disclosed herein are devices and methods for closing a hole in the wall of a cardiovascular structure from the inside using a self-assembling closure device. The closure device can be delivered to the subject hole from the inside of the cardiovascular chamber using a transcatheter approach. Disclosed techniques involve deploying the closure device from the delivery device such that an endo-cameral portion of the closure device self-expands first to cover the hole from the inside, and then extra-cameral arms of the device are released to self-deploy against the outside of the wall by
(Continued)

withdrawal of a retaining element, such as a guidewire, to secure the closure device to the wall.

35 Claims, 10 Drawing Sheets

(52) U.S. Cl.
CPC ............... *A61B 2017/00597* (2013.01); *A61B 2017/00606* (2013.01); *A61B 2017/00615* (2013.01); *A61B 2017/00623* (2013.01)

(58) Field of Classification Search
CPC ........... A61B 2017/00606; A61B 2017/00637; A61B 17/0644; A61B 17/12172; A61B 2017/00628; A61B 2017/00632; A61B 2017/00654; A61B 2017/00623; A61B 2017/00615; A61B 2017/00597; A61B 5/1459; A61B 17/00234; A61B 2017/00243; A61B 17/12122; A61B 2018/00351; A61B 5/1473; A61F 2002/016; A61F 2230/0069; A61F 2230/0093; A61F 2/01

See application file for complete search history.

(56) References Cited

U.S. PATENT DOCUMENTS

| | | |
|---|---|---|
| 2005/0070957 A1 | 3/2005 | Das |
| 2006/0276839 A1 | 12/2006 | McGuckin, Jr. |
| 2008/0071310 A1 | 3/2008 | Hoffman et al. |
| 2010/0234878 A1* | 9/2010 | Hruska ............... A61B 17/0057 606/213 |
| 2014/0074155 A1* | 3/2014 | Rothstein ........... A61B 17/0057 606/213 |
| 2015/0005810 A1* | 1/2015 | Center ............ A61B 17/12177 606/200 |
| 2016/0008002 A1* | 1/2016 | Dillard ............ A61B 17/12104 606/191 |

OTHER PUBLICATIONS

International Search Report and Written Opinion for related international Application No. PCT/US2016/054961, dated Dec. 8, 2016, 10 pages.

* cited by examiner

ENDO-CAMERAL CLOSURE DEVICE

CROSS-REFERENCE TO RELATED APPLICATIONS

This application is the U.S. National Stage of International Application No. PCT/US2016/054961, filed Sep. 30, 2016, which claims the benefit of U.S. Provisional Application No. 62/236,734, filed Oct. 2, 2015, which is incorporated by reference herein in its entirety.

FIELD

This application relates to devices and methods for closing a hole in the wall of a cardiovascular structure or other anatomical structure.

BACKGROUND

Some cardiovascular procedures include an intentional puncture of a wall in a cardiac chamber or blood vessel. For instance, the right atrial appendage is punctured in certain transcatheter procedures to allow a device to exit from within the right atrium into the pericardial space. Examples of such procedures include intra-pericardial heart valve annuloplasty and atrial appendage ligation. As another example, a hole can be created in the left ventricular apex during certain transthoracic mitral valve or aortic valve procedures. Other procedures can also result in a hole in the wall of a cardiac chamber or blood vessel, whether intentionally or accidentally.

If not closed quickly and safely, holes in the walls of cardiovascular structures can cause serious complications with high morbidity and mortality. One option is to surgically close such a hole. However, surgical closure techniques require access to the site of the hole, which may not be possible and/or can cause bystander injury to adjacent structures.

SUMMARY

Disclosed herein are devices and methods for closing a hole in the wall of a cardiovascular structure or other anatomical structure using a self-assembling closure device. In some methods, the closure device can be delivered to the subject hole from the inside of the cardiovascular chamber or vessel (endo-camerally) by using a transcatheter approach, while other methods involve delivering the closure device to the hole from the outside of a chamber. In some embodiments, a closure device is delivered via a transcatheter approach to the inside of a hole in the wall of cardiovascular structure, the catheter is advanced through the hole, and then the closure device is deployed from the catheter such that an endo-cameral portion of the closure device expands first to cover the hole from the inside and then extra-cameral portion of the device is deployed against the outside of the wall to secure the closure device to the wall. The closure device can be operated from one face of the wall without requiring access to both faces of the wall through which the whole extends. Operation and deployment of the device greatly facilitate endovascular procedures by reducing the number of instruments and access sites that are required.

During deployment of the closure device, a proximal endo-cameral occlusion member of the device can first be deployed inside the cardiovascular structure and can be positioned against an inner surface of the wall around the hole, and then distal extra-cameral portion of the closure device can be deployed against an outer surface of the wall by retracting a guidewire or other retaining element from the extra-cameral portion. The endo-cameral occlusion member of the closure device can resiliently self-expand when it is uncovered by an outer delivery sheath. The extra-cameral portion of the closure device can be retained by a guidewire or other retaining element passing through the catheter and through openings in the extra-cameral portion of the closure device, such that proximal withdrawal of the guidewire releases the extra-cameral portion to expand radially and shorten longitudinally to press against the outer surface of the wall after the inner portion of the closure device has already been deployed against the inner surface of the wall, creating a pinching force between the inner and outer portions of the closure device to maintain hemostatic sealing of the hole.

The foregoing and other objects, features, and advantages of the disclosed technology will become more apparent from the following detailed description, which proceeds with reference to the accompanying figures.

DETAILED DESCRIPTION

Explanation of Terms

Figure 1:
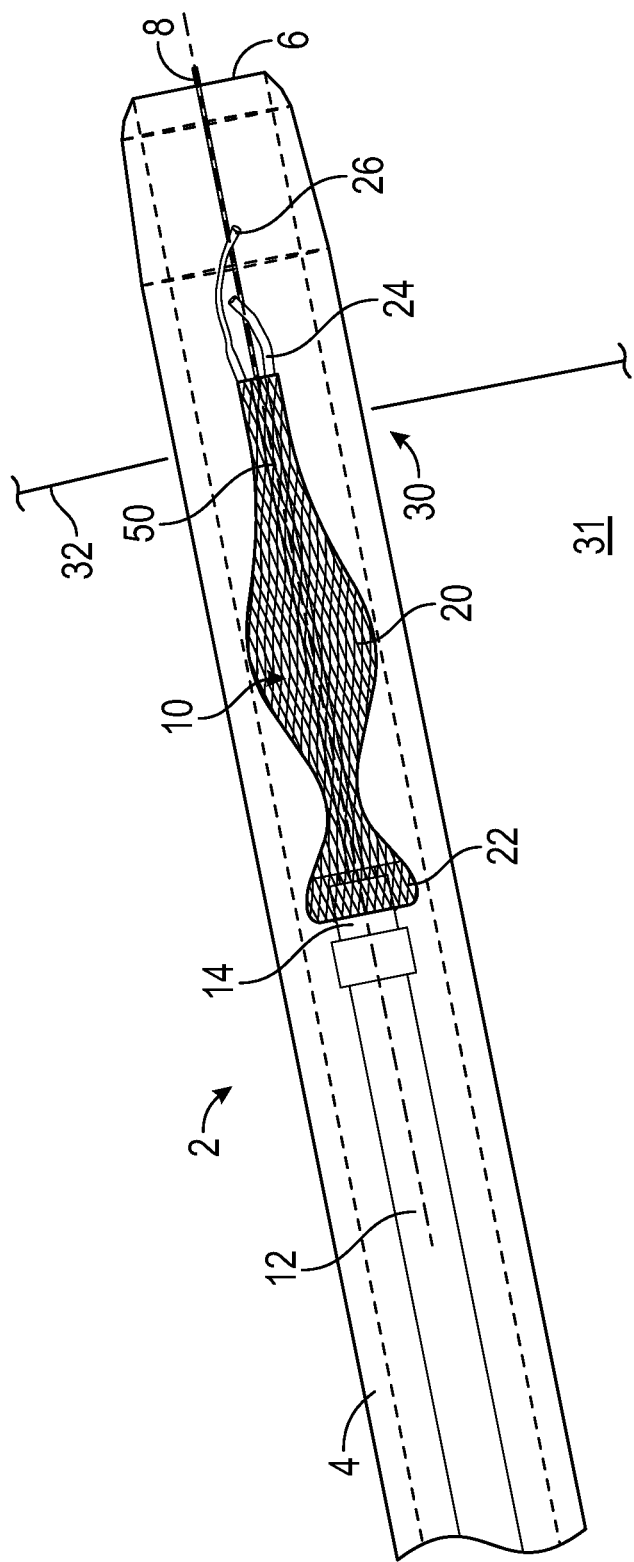
FIG. 1 is a side view of a distal portion of an exemplary transcatheter delivery device for delivering a closure device for closing a hole in a wall of a cardiovascular structure, showing the closure device disposed within the delivery device.

Unless otherwise noted, technical terms are used according to conventional usage. In order to facilitate review of the various embodiments of the disclosure, the following explanation of terms is provided.

The terms "distal" and "distally" refer to a location or direction that is, or a portion of a device that when inserted into the body (for example placed in a cardiovascular structure) is, farther away from the point of insertion into the body. For example, a leading end of a catheter is typically the distal end. The terms "proximal" and "proximally" refer to a location or direction that is, or a portion of a device that when inserted into the body is, closer to the point of insertion into the body. The term "longitudinal" refers to the axis extending in the distal and proximal directions, or to the longitudinal axis of a cylindrical body or lumen. The term "radial" refers to directions extending away from the longitudinal axis perpendicular to the longitudinal axis. The term "circumferential" refers to the directions extending around the longitudinal axis that are perpendicular to the longitudinal axis and at constant radius from the longitudinal axis.

As used herein, the term "endo-cameral" means within a cardiovascular structure, such as within a large blood vessel, within a cardiac chamber, or within an atrial appendage, or within another anatomical chamber or structure. By contrast, the term "extra-cameral" means outside of a cardiovascular structure or other anatomical chamber or structure. These terms are also used to describe an intended placement of a device with reference to a wall of the anatomical structure. For example, an endo-cameral occlusion member is intended to be placed inside of a cardiovascular structure adjacent an inner side of a wall of the cardiovascular structure, whereas an extra-cameral portion is intended to be positioned outside of the wall of the cardiovascular structure.

The singular terms "a", "an", and "the" include plural referents unless context clearly indicates otherwise. The term "comprises" means "includes without limitation." The term "coupled" means physically linked and does not exclude intermediate elements between the coupled elements. The term "and/or" means any one or more of the elements listed. Thus, the term "A and/or B" means "A", "B" or "A and B."

Although methods and materials similar or equivalent to those described herein can be used in the practice or testing of the present technology, only certain suitable methods and materials are described herein. In case of conflict, the present specification, including terms, will control. In addition, the materials, methods, and devices are illustrative only and not intended to be limiting.

Exemplary Methods, Devices, and Systems

Disclosed herein are devices and methods for closing a hole in the wall of a cardiovascular structure, or other anatomical structure, using a self-assembling closure device. The hole to be closed can be, for example, in the wall of a blood vessel or the heart. The hole can be anatomic, iatrogenic, or intentionally created for surgical, endovascular or endoscopic access. In some methods, the closure device can be delivered to the subject hole from the inside of the cardiovascular chamber or vessel, such as using a transcatheter approach, while in other methods the closure device is delivered to the hole from the outside of the chamber. Disclosed techniques involve delivering a closure device via a transcatheter approach to the inside of a hole in the wall of cardiovascular structure, advancing the catheter through the hole, and deploying the closure device from the catheter such that an endo-cameral portion of the closure device expands first to cover the hole from the inside and then extra-cameral arms of the device are deployed against the outside of the wall to secure the closure device to the wall. In some examples treatment includes creating the hole by perforating or otherwise penetrating the wall, for example, with a surgical or endovascular instrument, to establish the patency of the hole. In some examples, the hole is created to provide a temporary therapeutic access opening through the structure.

FIG. 1 is a side view of a distal portion of an exemplary delivery device 2 for deploying an exemplary closure device 10 to seal a hole 30 in a wall 32 of a cardiovascular structure. The delivery device 2 comprises an outer sheath 4 having a distal end 6 and a delivery catheter 12 positioned within the sheath 4. The closure device comprises a proximal endo-cameral occlusion member 20 and two distal extra-cameral arms 24, 26. The arms 24, 26 each have a base end portion coupled to a central portion of the occlusion member 20 and an engagement end portion 40, 42 at the free end of the arm.

A proximal portion 22 of the closure device 10 can be secured to a distal end portion 14 of the delivery catheter 12 so that the delivery catheter can be used to control the longitudinal placement of the device 10. The outer sheath 4 can be moved longitudinally relative to the delivery catheter 12 and the closure device 10 during deployment. The delivery device 2 with the closure device 10 inside can be advanced distally through the vasculature over a previously placed guidewire 8 that extends longitudinally through the center of the closure device 10, the delivery device 12, and the sheath 4.

The closure device 10 can be held in a radially compressed and longitudinally elongated delivery configuration (FIG. 1) when the closure device is positioned within the outer sheath 4, with the guidewire 8 passing through a central lumen 50 in the proximal occlusion member 20 of the closure device and passing through openings in the distal arms 24 and 26 of the closure device. In this delivery configuration, the closure device 10 can have a sufficiently small diameter to allow for transcatheter delivery through blood vessels to the location of the hole 30. For example, a hole in the right atrial appendage can be accessed by advancing the delivery device 2 through an access point in the femoral vein or other vein, through the inferior or superior vena cava, through the right atrium, and into the right atrial appendage. The guidewire 8 can be initially advanced through the delivery route and through the hole 30, and the delivery device 2 can then be advanced over the guidewire to and through the hole.

Figure 2:
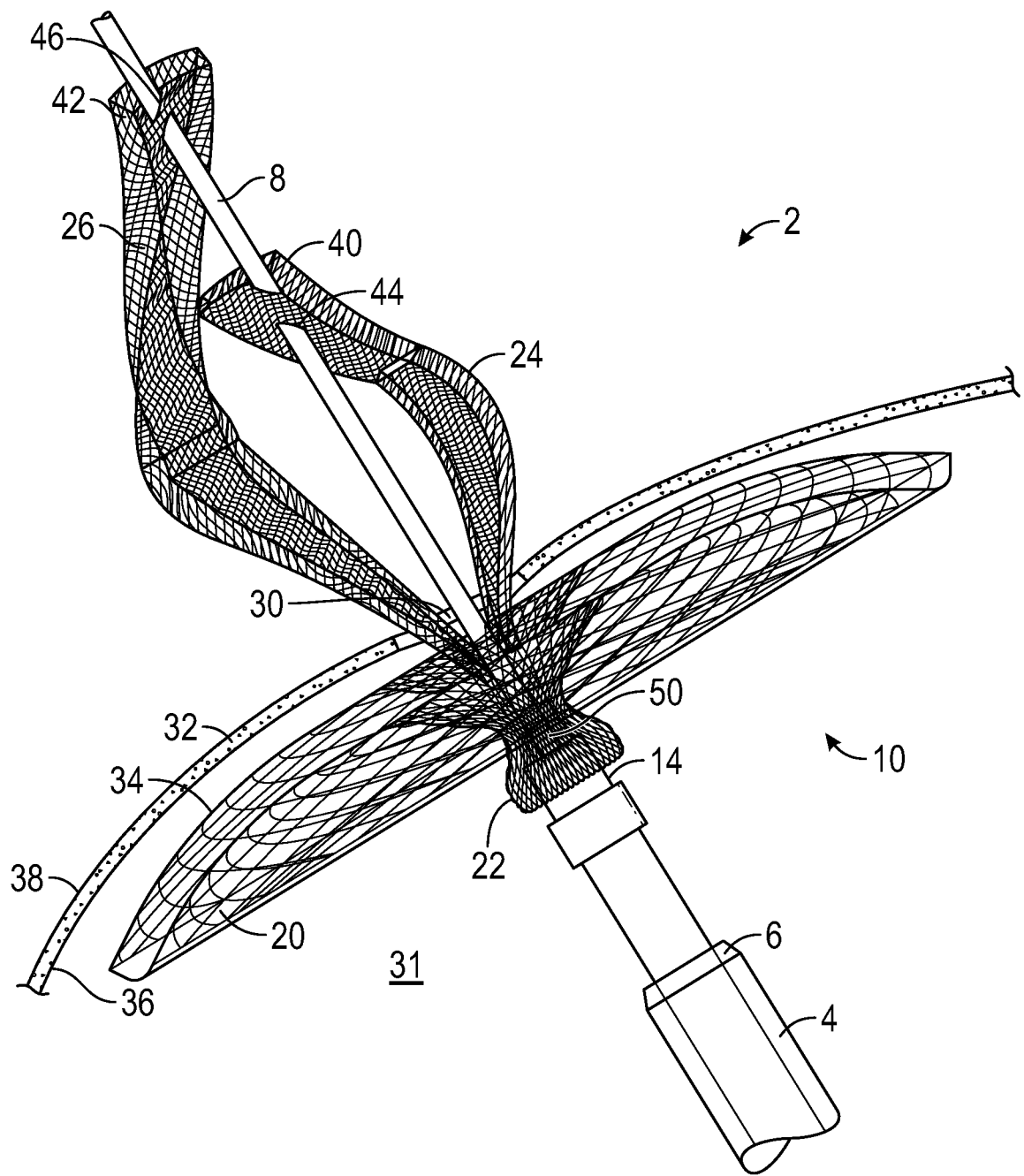
FIG. 2 is a side view showing the closure device partially deployed from the delivery device at a hole in a wall of a cardiovascular structure. An endo-cameral occlusion member of the closure device is deployed and positioned adjacent to an inner surface of the wall while extra-cameral arms of the closure device have not yet been deployed.
Figure 3:
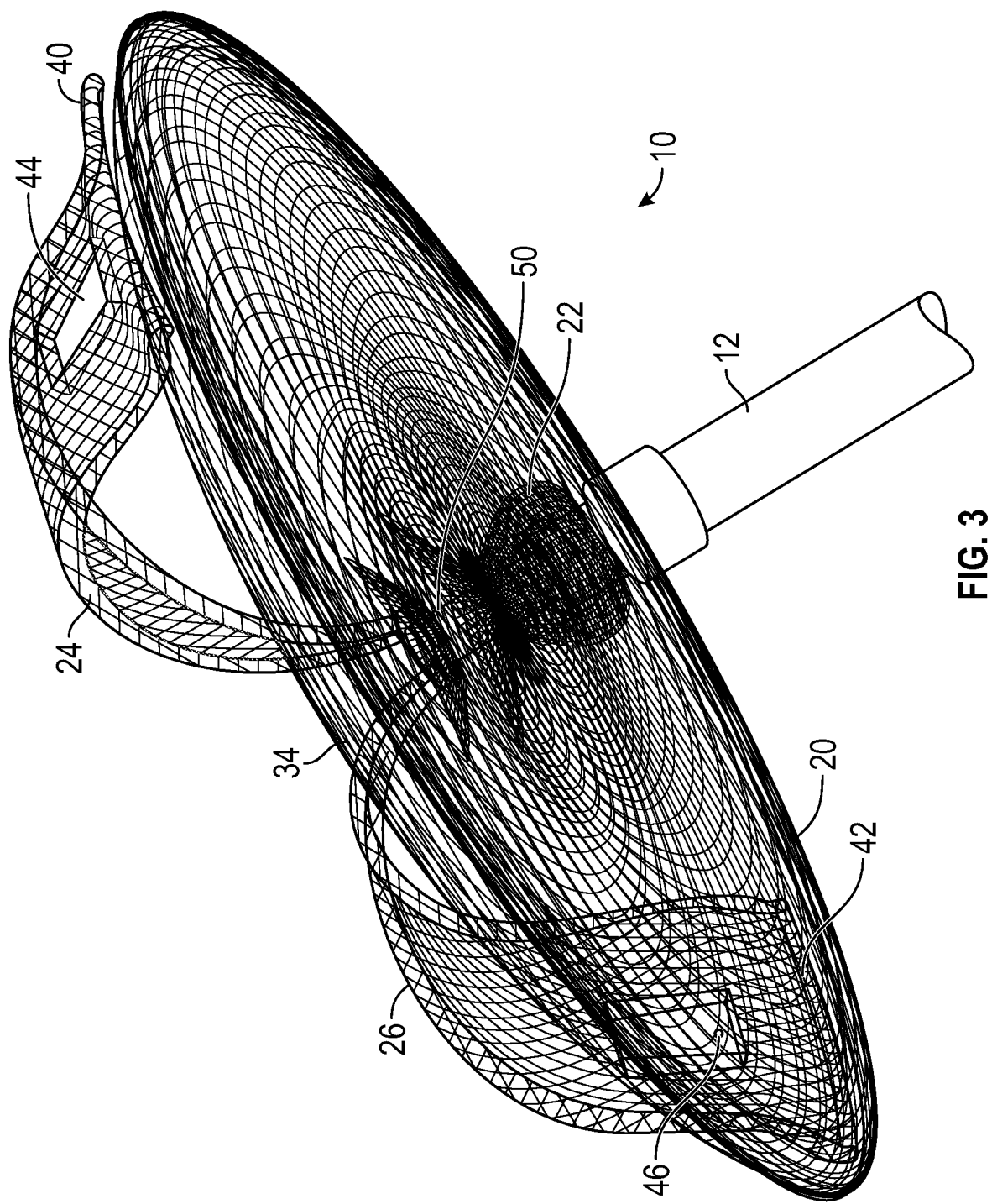
FIG. 3 is a perspective view showing the isolated closure device in a fully deployed configuration.
Figure 4:
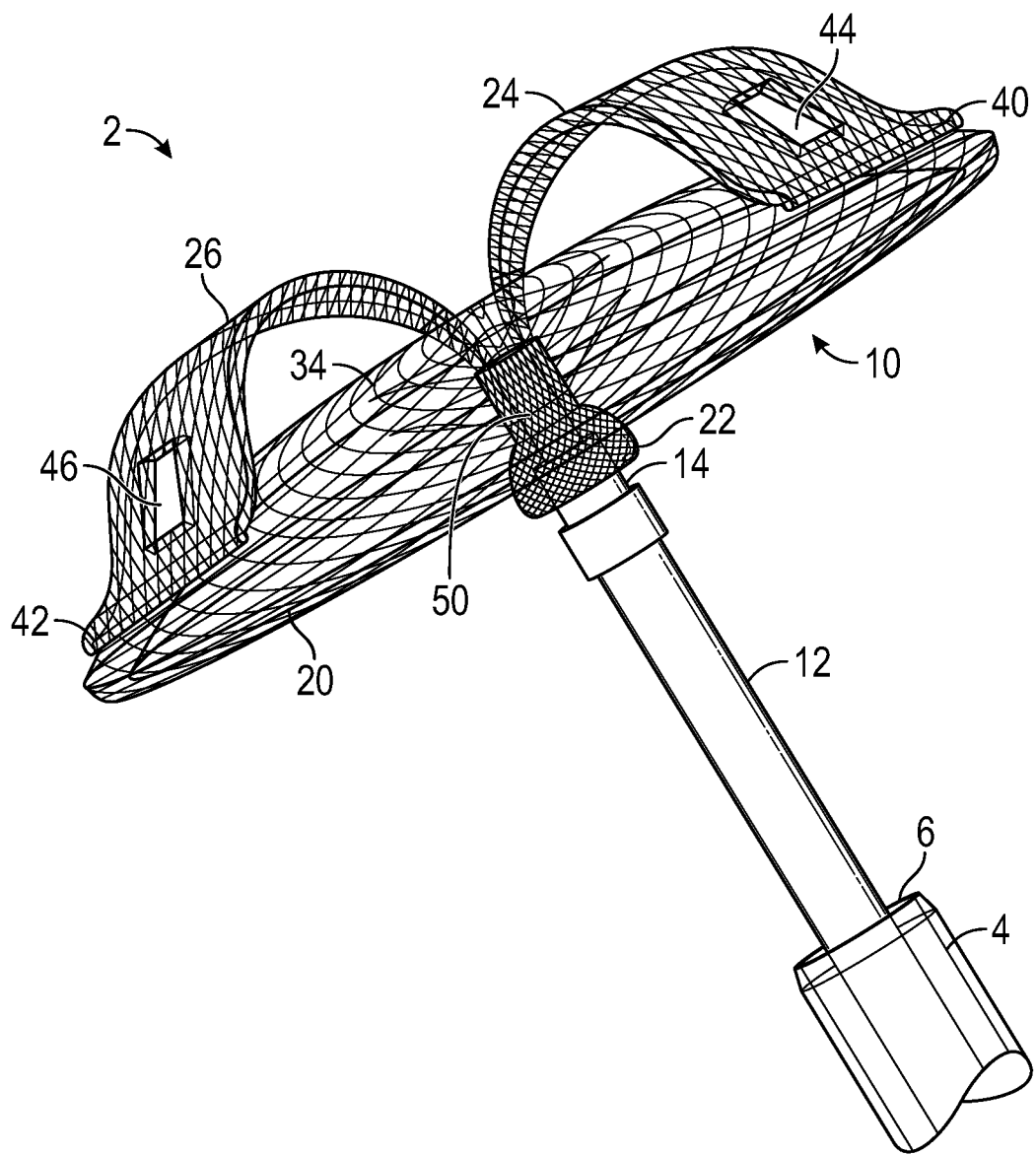
FIG. 4 is a side view showing the isolated closure device in a fully deployed configuration.
Figure 5:
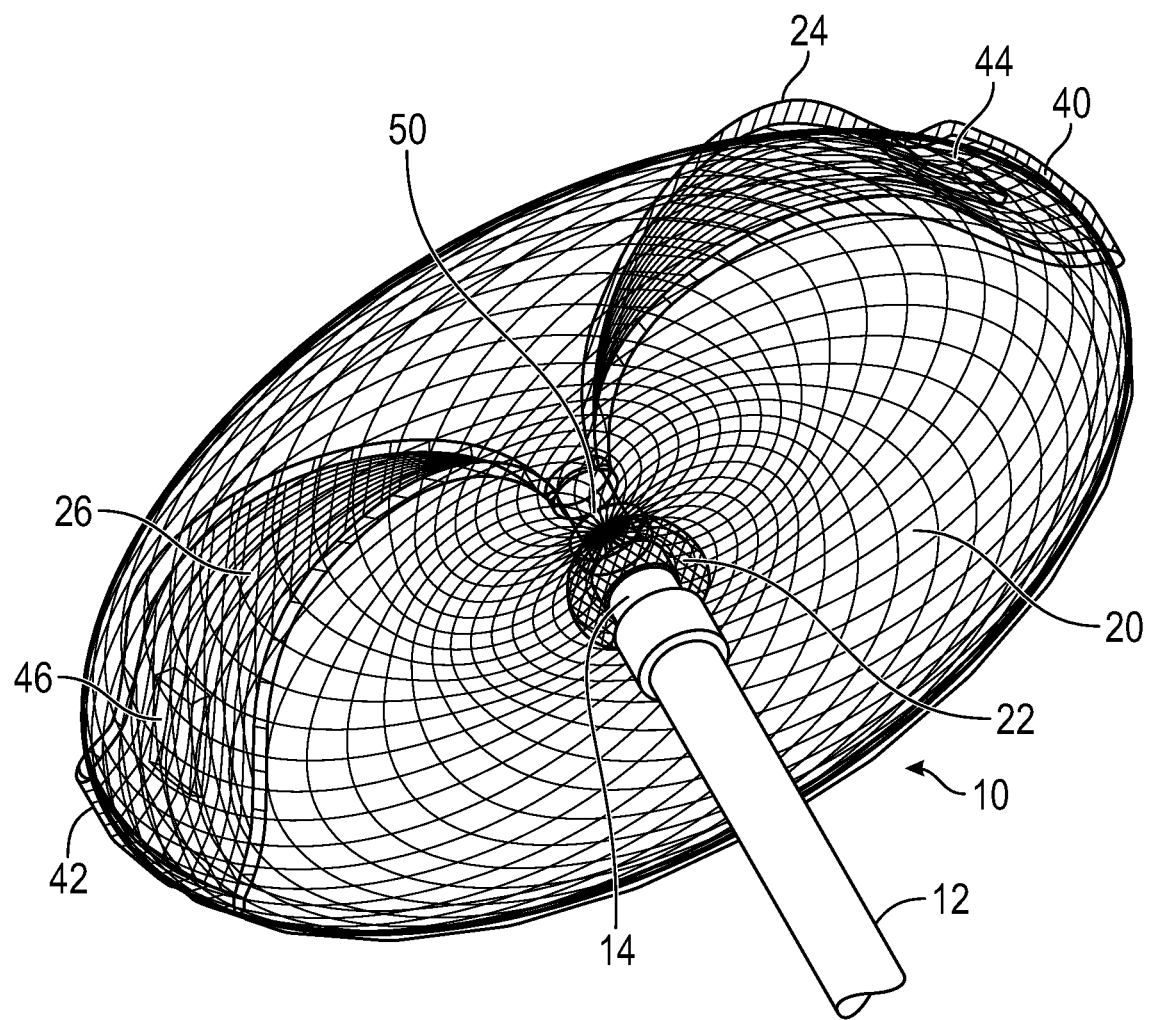
FIG. 5 is another perspective view showing a proximal aspect of the isolated closure device in a fully deployed configuration.

Once the delivery device 2 is positioned with the distal end of the sheath 4 extending through and/or adjacent the hole 30 to be closed, the outer sheath 4 can be retracted proximally relative to delivery catheter 12 and closure device 10. When the outer sheath 4 is retracted past the proximal end of the closure device 10, as shown in FIG. 2, the proximal endo-cameral occlusion member 20 of the closure device is allowed to radially self-expand to a deployment configuration having a disk-like shape, or other another preselected shape that conforms to the general shape of the inner surface of the structure through which hole 30 extends. For example, the occlusion member can have an arcuate shape that conforms to the curved endothelial surface of a blood vessel or cardiac structure.

As shown in FIG. 2, the expanded occlusion member 20 can be deployed adjacent to an inner surface 36 of the cardiovascular wall 32 that includes the hole 30, with the distal arms 24, 26 extending through the hole 30. In alternative embodiments, an additional intermediate member can extend between the base ends of the arms and the occlusion member, and the intermediate portion can extend through the hole, with the arms being positioned entirely outside of the hole. The intermediate portion can comprise a cylindrical body, for example.

The distal arms 24, 26 are still retained by the guidewire 8 passing through openings 44, 46 in the respective arms, as shown in FIG. 2. The engagement of the guidewire 8 through the openings 44, 46 keeps the distal arms 24, 26 in a radially compressed and longitudinally elongated state and keeps them from resiliently curling radially outwardly and proximally to engage with the outer surface 38 of the wall 32 around the hole 30.

In an alternative embodiment, one or more retainer elements other than, or in addition to, the guidewire 8 can be used to retain the distal arms 24, 26 in the delivery configuration. For example, a semi-rigid rod can be positioned extending through the openings 44, 46, and the rod can be retracted proximally to deploy the arms. Such a rod can be more rigid than the guidewire 8 to provide better control over the retaining and deployment of the arms. The retainer elements can extend in parallel with the guidewire 8, for example. In some embodiment, two different retainer elements can be used, with one engaged with the arm 24 and the other engaged with the arm 26. This can allow deployment of either arm first. When another retainer element is used to retain the arms 24, 26, the guidewire 8 may or may not pass through the openings 44, 46. Use of a retainer element other than the guidewire 8 can also allow deployment of the arms without retraction of the guidewire, which can facilitate future advancement of the delivery device and/or closure device back over the guidewire.

In the partially deployed configuration of FIG. 2, the closure device 10 can be positioned as desired to place the expanded endo-cameral occlusion member 20 over the hole 30 against the inner surface 36 of the wall 32. The occlusion member 20 can be at least as large as the hole 30 so that it can form a sealing engagement with the tissue all the way around the hole.

Figure 6:
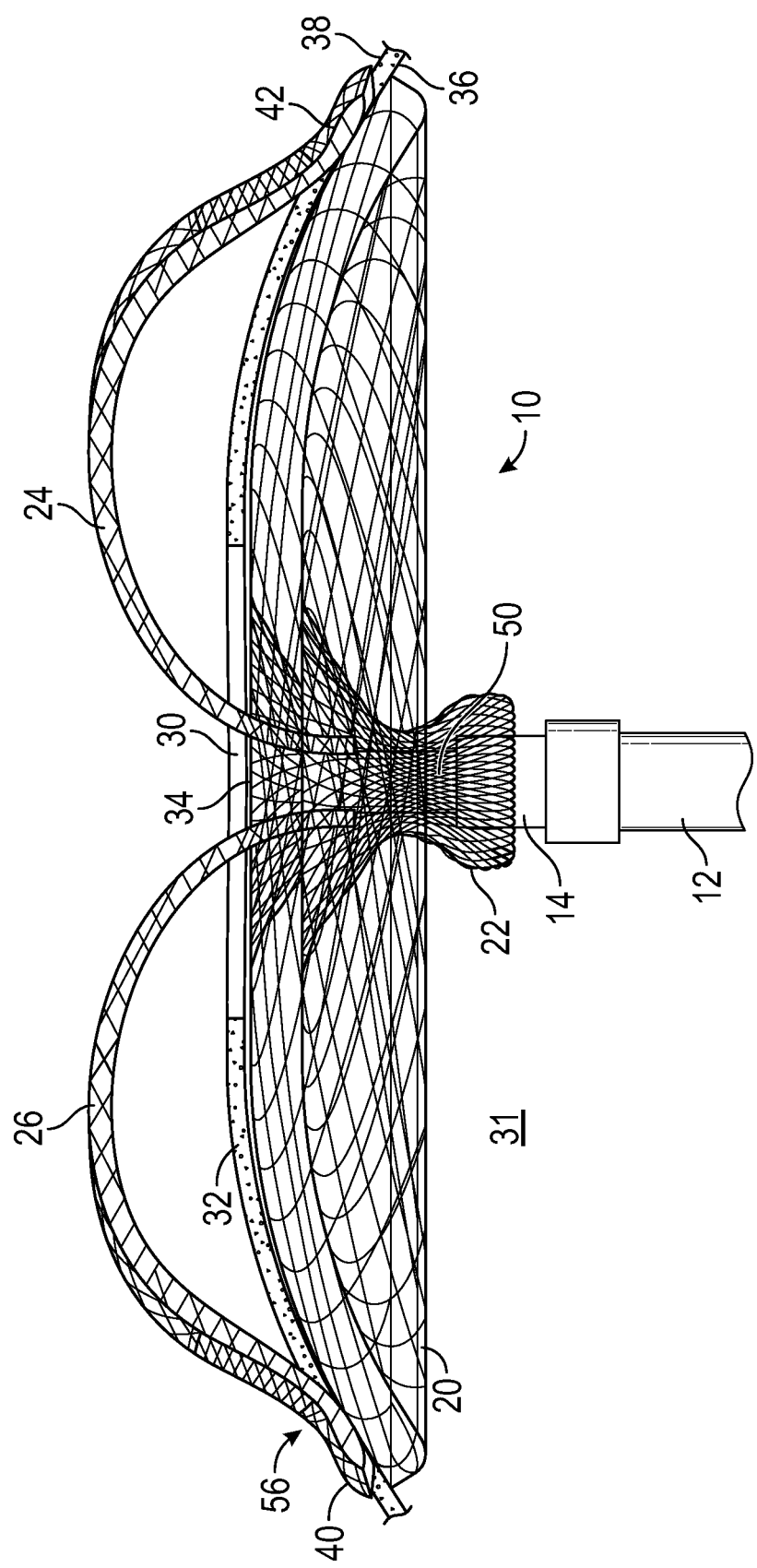
FIG. 6 is another side view showing the closure device in a fully deployed configuration sealing a hole in a wall of a cardiovascular structure.
Figure 7:
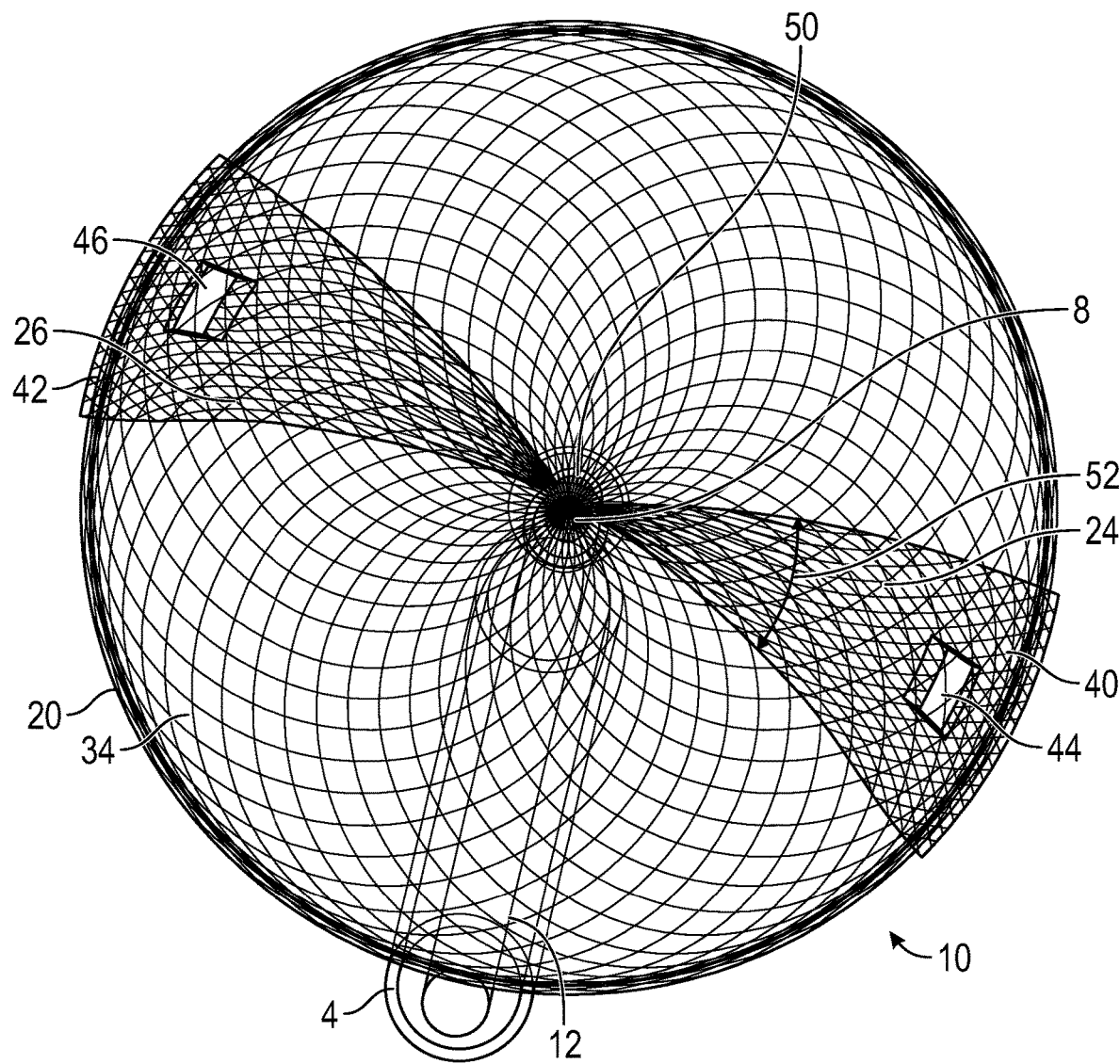
FIG. 7 is another perspective view showing a distal aspect of the closure device in a fully deployed configuration.

Once the occlusion member 20 is positioned as desired adjacent the inner surface 36 of the wall 38, the guidewire 8 can be retracted proximally through the openings 44, 46 in the distal portions 24, 26. The guidewire 8 can optionally be retracted proximally all the way through the central lumen 50 in the occlusion member 20 and into the delivery catheter 12. As shown in FIGS. 3-7, once free from the guidewire 8, the distal arms 24, 26 resiliently bend or curl apart from each other such that the engagement portions 40, 42 move radially outwardly and proximally toward the perimeter of the occlusion member 20. This process can be referred to as self-assembly or self-deployment of the arms. As shown in FIG. 6, the engagement portions 40, 42 pinch the wall 32 against the opposing surface 34 of the occlusion member 20 to secure the closure device 10 to the wall.

In the deployed configuration shown in FIG. 6, the occlusion member 20 is held tight against the wall 32 to form a seal around the hole 30 and prevent or substantially restrict blood flow out through the hole. High pressure within the cardiovascular chamber or vessel can enhance the sealing effect by urging the occlusion member outwardly against the inner surface of the wall around the hole. This central lumen 50 of the occlusion member 20 can resiliently seal itself once the guidewire 8 is removed.

Once the closure device 10 is secured to the wall as shown in FIG. 6, the delivery catheter 12 can be detached from the closure device 10. For example, the distal end portion 14 of the delivery catheter 12 can be separated from the proximal end portion 22 of the closure device 10. The outer sheath 4, delivery catheter 12, and guidewire 8 can then be retracted proximally out of the body.

The closure device 10 can comprise a resiliently deformable material such that it can be deformed from a natural configuration (similar to that shown in FIGS. 3-7) into a radially compressed delivery configuration (as shown in FIG. 1), and then resiliently return toward the natural configuration when freed from restricting external forces. For example, the closure device 10 can comprise superelastic or "shape memory" material, such as nitinol, flexinol, titanium-palladium, platinum alloys, and/or other metal alloy materials. Other elastic or superelastic materials can also be used, such as polymeric and/or metallic materials.

The material of the closure device 10 can be deformed sufficiently to fit into the sheath 4 for transvascular delivery through narrow blood vessels and/or through narrow holes to be closed. The material of the closure device 10 can retain its resiliency while in the radially compressed and elongated delivery configuration such that when released from the restraints of the sheath 4 and the guidewire 8 the closure device 10 resiliently returns to or toward its natural configuration to pinch the wall around the hole to be closed. In the fully deployed configuration of FIG. 6, the distal arms 24, 26 arc away from and then back toward the occlusion member 20 to maintain at least some biasing force that urges the engagement end portions 40, 42 of the arms against the wall 30 opposite the occlusion member 20. With this inherent clamping force, the closure device 10 can ensure secure apposition to the wall 30 regardless of the thickness of the wall.

The occlusion member 20 of the closure device 10 can comprise a lattice or mesh type structure composed of interwoven strands or filaments of resiliently deformable material. The lattice or mesh type structure can allow the occlusion member to move between the radially compressed and axially elongated configuration shown in FIG. 1 during delivery, and the radially expanded and axially shortened configuration shown in FIGS. 2-7 when deployed. Furthermore, in some embodiments a blood impervious coating or liner can be included on the occlusion member 20 to enhance the hemostatic effect after delivery.

In some embodiments, occlusion member 20 can include a sealing material or surface that contacts tissue around the hole and helps seal against the tissue to restrict blood from flowing out of the higher pressure chamber or vessel between the closure device and the native tissue. In some embodiments, the sealing material or surface can comprise gasket-like qualities, such as being pliant, elastomeric, and/or resiliently deformable to conform to the native tissue wall around hole. More information regarding the materials, structures, and functionality of cardiovascular closure devices, and the occlusion member 20 in particular, and related methods of use, can be found in WO 2015/020682, which is incorporated by reference herein in its entirety.

The distal arms 24, 26 can comprise resiliently deformable material, such as solid or mesh material. Each of the arms can comprise an elongated body having a free end and a fixed end or base end coupled to the occlusion member 20 at a radially central location adjacent the central lumen 50. The distal arms 24, 26 can generally increase in circumferential width (see dimension 52 in FIG. 7) moving from the fixed end adjacent the central lumen 50 toward the engagement portions 40, 42. The increased width of the engagement portions 40, 42 can distribute pinching pressure to enhance the sealing effect and minimize the risk of damaging the tissue wall that is pinched. Once deployed, each arm assumes an arcuate configuration that curves away from wall 32 to a vertex (high point in FIG. 6) and then continues to curved back toward wall 32. As shown in FIG. 6, for example, the distal arms 24, 26 can also curve radially outwardly (see arrow 56 in FIG. 6) in the area of the engagement portions 40, 42 such that the engagement portions press against the wall tissue generally parallel with the opposing surface of the occlusion member 20, which also helps to reduce pressure concentrations when the closure device is pinched onto a tissue wall.

In the deployed configuration with the engagement ends of the arms pressed against the outside of the wall, the arms and/or other portions of the closure member still retain a resilient, elastic force that urges the arms and the occlusion member toward each other so that they pinch the wall. In this manner, the arms act as clips or springs to apply orthogonal counterpressure to the occlusion member and the wall therebetween, and thereby retain the closure device on the wall and closing the hole. Even when not pinching a wall, such as when allows to assume the deployed configuration outside of the body, the arms can still pinch against the occlusion member with substantial resilient force. This ensures the pinching force is present and sufficient no matter how thick the wall containing the hole is.

In some embodiments, the closure device can be sized and operable to close holes as small as 1.0 mm in diameter, or smaller, and/or as large as 6 mm in diameter, or larger. Some embodiment are configured to close holes up to 10 mm and/or up to 15 mm in diameter.

The arms can have lengths, from their base ends to their free engagement ends, as small as 3 mm, or shorter, and/or as long as 20 mm, or longer. The length in some embodiments is greater that the radius of the deployed occlusion member.

The two arms 24, 26 can have different lengths. For example, as shown in FIG. 1, arm 24 can be shorter that arm 26. In some embodiments, the arms 24, 26 are coupled to the guidewire 8 at two different longitudinal locations. For example, as shown in FIG. 1, the arm 24 is coupled to the guidewire at a location that is proximal to where the arm 26 is coupled to the guidewire. In some embodiments, the arms can have the same linear length, but one arm can be bend or deformed more than the other in the delivery configuration such that the two arms attach the guidewire at different longitudinal positions. In some embodiments, the openings 44, 46 can be positioned at different points along their respective arms 24, 26 to allow the two arms to be coupled to the guidewire at different longitudinal positions, whether or not the arms have the same overall length.

In some embodiments, the engagement arms can have a width as narrow as 1.5 mm, or smaller, and/or as broad as 5 mm, or larger. In some embodiments, the engagement ends of the arms can have a width as broad as half the circumference of the deployed occlusion member. The width can increase moving from the base end to the free engagement end (e.g., from 1.5 mm at base to 5 mm at free end), or can be constant along the length of the arms, or can have other variable width profiles. In some embodiments, the arms have a petal shape, leaf shape, oval shape, triangular shape, trapezoidal shape, rectangular shape, hemispherical shape, sector shape, pie-slice shape, or other shape, when flattened.

In the deployed configuration, the arms can form an arcuate shape that has a radius of curvature as small as 3 mm, or less, and/or a radius of curvature as large as 18 mm, or greater. The radius of curvature can gradually change along the length of the arms, for example being smallest at or near the apex of the curvature and/or near the a radially outward bend adjacent the engagement end portions.

In some embodiments, the closure device 10 can include only one, or three or more, of the distal arms. For example, three distal arms can be arrayed about 120° apart circumferentially or four distal arms can be arrayed about 90° apart circumferentially. In embodiment with three or more arms, the various arms can each be coupled to the guidewire at different longitudinal positions in the delivery configuration, or can be coupled to more than one different retaining element.

In some embodiments, the closure device 10 can be recaptured and/or repositioned after an initial incorrect placement. For example, the closure device 10 can be recaptured by advancing the sheath 4 or another tubular device distally over the deployed device 10 to cause the device or a portion thereof to radially compress and move back into the sheath 4 or another tubular device. Once re-captured, the closure device can be repositioned and redeployed, or can be retracted out of the body and optionally re-inserted or replaced with another closure device.

The disclosed technology can be used to close various different sizes of holes in various different cardiovascular structures using various different transcatheter delivery approaches. Furthermore, the hole to be closed can be intentionally created for another procedure, can be accidentally created, or can be naturally present (e.g., birth defect, ruptured aneurism, etc.).

Exemplary cardiovascular structures that may include a hole in a wall that can be closed using the disclosed technology include the right atrium, right atrial appendage, right ventricle, left atrium, left atrial appendage, left ventricle, superior vena cava, inferior vena cava, pulmonary arteries, pulmonary veins, aorta, and other blood vessels.

Exemplary procedures that may result in a hole that can be subsequently closed using the disclosed technology include transatrial intrapericardial tricuspid and mitral valve annuloplasty (see, e.g., WO 2014/159842 and WO2014/200764, which are incorporated by reference herein in their entireties), transatrial left and right atrial appendage ligation (see, e.g., WO2015/061775, which is incorporated by reference herein in its entirety), transatrial access for other procedures such as pericardial insufflation and ablation (see, e.g., Rogers et al., "Intentional right atrial exit for microcatheter infusion of pericardial carbon dioxide or iodinated contrast to facilitate sub-xiphoid access", Catheterization and Cardiovascular Interventions, 2015 August; 86(2):E111-8; (PMID:25315516) and Greenbaum et al., "Intentional right atrial exit and CO2 insufflation to facilitate subxiphoid needle entry into the empty pericardial space: first human experience", JACC Clinical Electrophysiology, 2015; which are incorporated by reference herein in their entireties), and various procedures for accessing and treating the mitral valve or aortic valve via transcatheter access through a hole in or near the apex of the left ventricle or through a hole in the septum.

Depending on the location of the hole to be closed, the disclosed technology can be delivered to the hole location using various different delivery routes. For example, holes in the right atrium or right atrial appendage can be accessed via a transfemoral route through the femoral artery and inferior vena cava, or via the jugular, axillary or subclavian veins and the superior vena cava. Holes in the left side of the heart may be accessed via a transfemoral route through a femoral artery and aorta, or through a femoral vein and inferior vena cava and across a caval-aortic crossing to the aorta, or from other vascular access points. Holes in the apex of the left ventricle can be accessed through the aorta and through the aortic valve, or through the left atrium and mitral valve, or via external transthoracic access routes.

Figure 11:
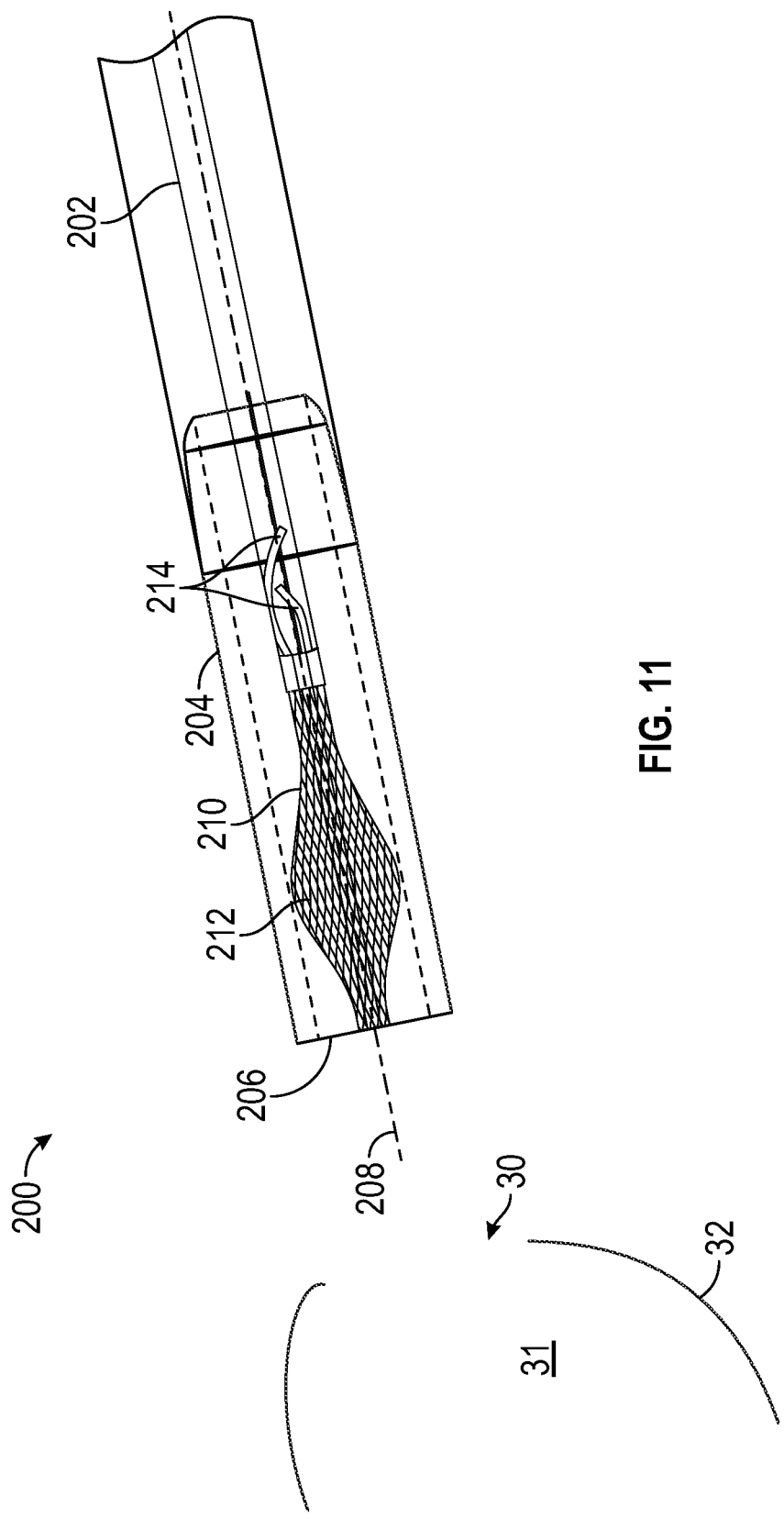
FIG. 11 is a side view of another alternative embodiment for delivering a closure device to a hole from outside of the hole. In this embodiment, the closure device is contained within a delivery device with the endo-cameral occlusion member positioned distal to the extra-cameral arms.
Figure 12:
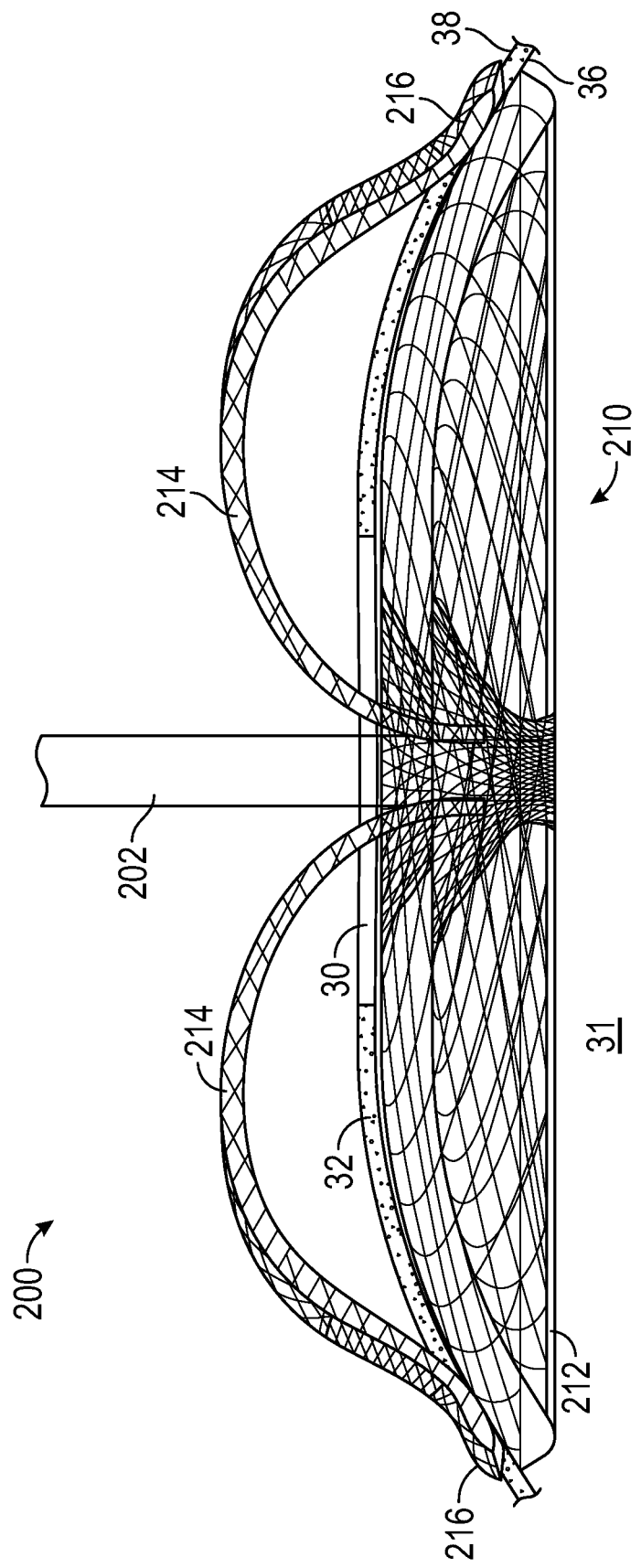
FIG. 12 is a side view of the closure device of FIG. 11 after being delivered from outside of a hole and fully deployed to seal the hole.

As illustrated in FIGS. 11 and 12, disclosed closure devices can also be delivered to a hole in a chamber and deployed from the outside of the chamber. In such methods, the orientation of the closure device can be flipped around inside of the delivery sheath, with the endo-cameral occlusion member being positioned distal to the extra-cameral portion. As shown in FIG. 11, a delivery device 200 carrying a closure device 210 can be advanced so that a distal end 206 of an outer sheath 204 approaches the outside of a wall 32 with the hole 30 in it, and the distal end 206 of the sheath can be advanced through the hole 30 into the chamber 31. The closure device 210 is oriented with the endo-cameral occlusion member 212 distal to the extra-cameral arms 214. An inner delivery catheter 202 positioned inside the outer sheath 204 can be coupled to a proximal part of the closure device 210. A guidewire 208 can pass through inner delivery catheter 202, through openings in the arms 214, through the occlusion member 212, and can extend from the distal end 206 of the device and into the hole 30.

Once the distal end 206 in inserted through the hole 30 into the chamber 31, the sheath 204 can be retracted and/or the closure device 210 advanced, such that the distal occlusion member 212 is released from the distal end 206 of the sheath inside of the chamber 31, allowing the occlusion member to self-expand inside the chamber while the arms 214 remain in a radially compressed state, either still inside of the sheath 204 or not. The arms 214 can be retained in the radially compressed state by a retaining element (e.g., guidewire 208) passing through holes in the arms, such that the arms remain in the compressed state even after the sheath 204 is retracted from the entire closure device 210. After the occlusion member 212 is expanded and placed into sealing contact with the inner surface 36 of the wall 32 around the hole 30, the guidewire 208 can be retracted to allow the arms 214 to deploy and cause engagement ends 216 of the arms to pinch against the outer surface 38 of the wall 32, as shown in FIG. 12. The inner delivery catheter 202 can then be detached from the device 210 and removed. In one example, such a delivery and deployment from the outside of the hole can be used to close a hole in the apex of the left ventricle using a transthoracic delivery approach through the pericardium to the apex of the heart.

Figure 8:
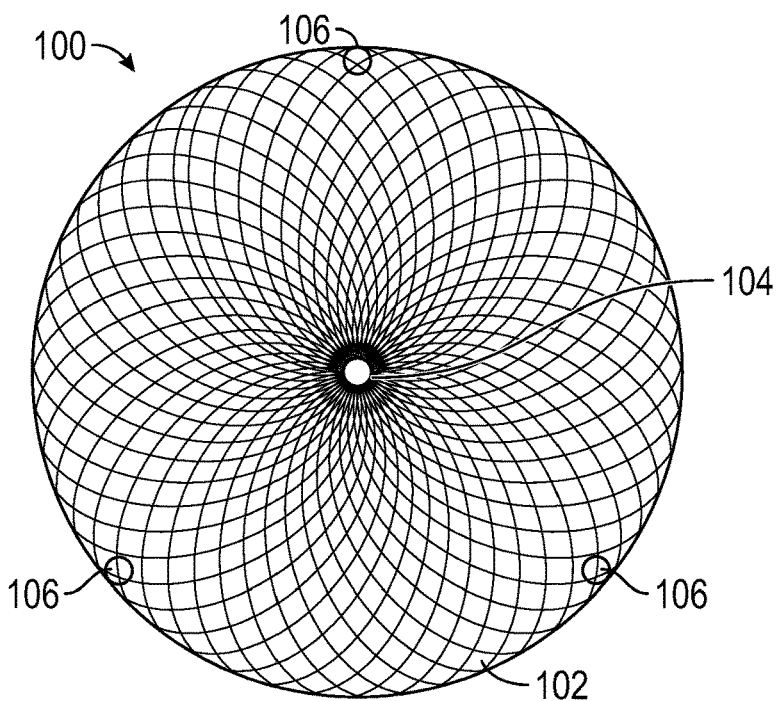
FIG. 8 is an end view of a radially expanded, disk-shaped extra-cameral portion of an alternative closure device.
Figure 9:
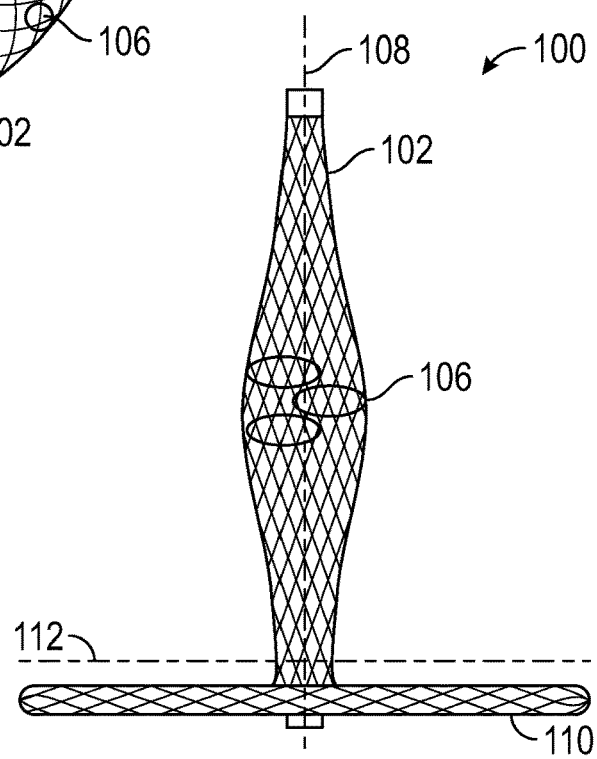
FIG. 9 is a side view of the closure device of FIG. 8, showing the extra-cameral portion being held by a guidewire in a radially collapsed configuration outside of a hole to be closed, and a disk-shaped endo-cameral portion radially expanded and positioned inside of the hole.
Figure 10:
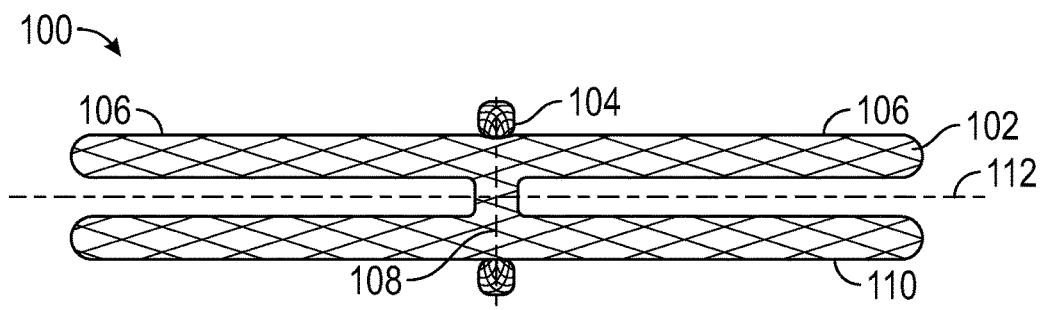
FIG. 10 is a side view of the closure device of FIG. 9, showing the extra-cameral portion after it is radially expanded to a disk-shaped deployment configuration.

FIGS. 8-10 illustrate an alternative closure device 100 that includes a disk-shaped extra-cameral portion 102 instead of individual arms. The extra-cameral portion 102 is radially compressible and self-expandable. As shown in FIG. 8, the extra-cameral portion 102 includes openings 106 (e.g., two, three, or more) near the radial perimeter when in the radial expanded state and a central opening 104. When radially collapsed, as shown in FIG. 9, the openings 106 are brought together near the center of the extra-cameral portion, and the guidewire 108 (or other retaining member) passes through the openings 106 (see FIG. 9) to hold the extra-cameral portion 102 in the radially collapsed state. The guidewire 108 also passes through the central opening 104 and through the endo-cameral portion 110. Like other closure devices disclosed herein, the endo-cameral portion 110 is deployed first inside the chamber while the extra-cameral portion 102 is held radially collapsed outside of the 112 containing the hole to be closed, such that the device 100 extends through the hole. After the expanded occlusion member 110 is placed into contact with the inner surface of the wall 112, the guidewire 108 is retracted from the openings 106, allowing the extra-cameral portion 102 to self-expand to the disk-shaped deployment form, as shown in FIG. 10, and pinch the wall 112 between the two disk-shaped portions 110 and 102, thereby sealing the hole. The device 100 can be delivered from either inside the hole or from outside the hole, using delivery devices and methods analogous to those described elsewhere herein.

Delivery, placement, and deployment of the disclosed closure devices can be performed using various imaging techniques to visualize the relative location of the delivery device and closure device. In some embodiments, radiopaque bands or elements can be included on the delivery device and/or on the closure device to enhance radiographic imaging.

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and sub-combinations with one another. The methods, devices, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim at least all that comes within the scope of these claims.

The invention claimed is:

1. A device for closing a hole in a wall of a cardiovascular structure, comprising:
   an endo-cameral occlusion member configured to seal against an inner surface of a wall of a cardiovascular structure around a hole in the wall, the occlusion member comprising a resiliently deformable material and configured to be radially compressed to a delivery configuration for transcatheter delivery to within the cardiovascular structure adjacent the hole and configured to radially self-expand to a deployment configuration when released from within a delivery sheath; and
   first and second extra-cameral arms coupled to the occlusion member and configured to engage an outer surface of the wall in a deployed configuration to secure the device to the wall, the arms each comprising a base end portion coupled to the occlusion member, an engagement end portion configured to contact the outer surface of the wall when deployed, and an opening that receives a retaining element that retains the arms in a radially compressed delivery configuration, wherein the arms comprise a resiliently deformable material and are configured to be held in the radially compressed delivery configuration during transcatheter delivery and during deployment of the occlusion member, wherein the arms comprise a mesh material, and wherein the arms are configured to resiliently self-expand to a deployment configuration after the occlusion member has self-expanded to its deployment configuration when the retaining element is removed from within the openings in the arms.

2. The device of claim 1, wherein the closure device is configured to be delivered through the cardiovascular system to approach the hole from inside of the cardiovascular structure.

3. The device of claim 1, wherein the retaining element is a guidewire of a transcatheter delivery device, and the guidewire is removed from within the openings in the arms by proximal withdrawal of the guidewire.

4. The device of claim 1, wherein the openings are located in or adjacent the engagement end portions of the arms.

5. The device of claim 1, wherein the arms are longitudinally elongated extending away from the occlusion member in the delivery configuration.

6. The device of claim 1, wherein the arms curl or fold radially outwardly and back toward the occlusion member when released from the retaining element.

7. The device of claim 1, wherein the arms increase in width from the base end portion toward the engagement end portion.

8. The device of claim 1, wherein the base end portions of the arms are coupled to a radially central portion of the occlusion member.

9. The device of claim 1, wherein the engagement end portions of the arms curve radially outwardly in the deployed configuration such that a broad surface of the engagement end portions contact the outer surface of the wall.

10. The device of claim 1, wherein arms extend in opposite radial directions from each other in the deployed configuration.

11. The device of claim 1, wherein the first arm is longer than the second arm.

12. The device of claim 1, wherein the first arm engages the retaining member at a different longitudinal position than where the second arm engages the retaining member.

13. The device of claim 1, wherein the occlusion device forms a disk shape in the deployed configurations.

14. The device of claim 1, wherein the occlusion device includes a central lumen through which the retaining element extends.

15. The device of claim 1, wherein the occlusion device comprises a mesh of thin elongated strands.

16. The device of claim 1, wherein the occlusion device shortens longitudinally as it expands radially.

17. The device of claim 1, wherein the occlusion device comprises a sealing material on a surface that engages the inner surface of the wall to enhance hemostatic sealing around the hole.

18. The device of claim 1, wherein the arms pinch the wall against the occlusion device to retain the device to the wall with the occlusion device sealing the hole in the wall.

19. A system comprising the closure device of claim 1 in combination with a delivery device configured to deliver the closure device in a radially compressed state to a hole in a wall of the a cardiovascular structure and configured to deploy the closure device to close the hole.

20. The system of claim 19, wherein the delivery device comprises a guidewire that extends through a lumen in the endo-cameral occlusion device and through openings in the extra-cameral arms in a delivery configuration.

21. The system of claim 20, wherein the guidewire retains the arms in a delivery configuration and releases the arms upon retraction of the guidewire from the openings in the arms to allow the arms to self-deploy against an outer surface of the wall.

22. The system of claim 19, wherein the delivery device is configured to contain the closure device in a radially compressed state during delivery with the endo-cameral occlusion member of the closure device positioned proximal to the extra-cameral arms.

23. The system of claim 19, wherein the delivery device is configured to contain the closure device in a radially compressed state during delivery with the endo-cameral occlusion member of the closure device positioned distal to the extra-cameral arms.

24. A method of closing a hole in a wall of a cardiovascular structure, comprising:
   advancing a delivery device through the a patients anatomy to position a distal end portion of the delivery device extending through a hole in a wall of a cardiovascular structure, the delivery device carrying a closure member in a radially compress state within a sheath;
   retracting the sheath proximally to uncover the closure device and thereby allowing an endo-cameral occlusion member of the closure device to radially self-expand within the cardiovascular chamber while extra-cameral arms of the closure device remain in a radially compressed state positioned outside of the hole;
   positioning the expanded occlusion member against or adjacent to an inner surface of the wall covering the hole in the wall; and
   retracting a retaining element of the delivery device proximally from engagement with the extra-cameral arms to allow the arms the curl or bend radially outwardly and toward the occlusion member such that engagement end portions of the arms contact an outer surface of the wall and pinch the wall between the arms and the expanded occlusion member, wherein the arms comprise a mesh material and each arm has an opening that receives the retaining element.

25. The method of claim 24, wherein retracting the retaining element comprises retracting a guidewire such that the guidewire no longer extends through openings in the arms.

26. The method of claim 24, wherein advancing a delivery device through the a patient's anatomy comprises advancing the delivery device through the cardiovascular system to approach the hole from inside of the cardiovascular chamber and passing the distal end portion of the delivery device through the hole in the wall out of the cardiovascular structure.

27. The method of claim 26, wherein advancing the delivery device through the cardiovascular system comprises advancing the delivery device through the venous system, into the right atrium, into the right atrial appendage, and through a hole in the right atrial appendage into the pericardial space.

28. The method of claim 24, wherein advancing a delivery device through the a patient's anatomy comprises approaching the hole from outside of the cardiovascular chamber and passing the distal end portion of the delivery device through the hole in the wall into the cardiovascular structure.

29. The method of claim 24, further comprising re-advancing the sheath distally over the closure device after the closure device is deployed to re-capture the closure device within the sheath.

30. The method of claim 24, further comprising initially creating the hole in the wall of the cardiovascular structure to allow passage of a treatment device through the wall of the cardiovascular structure.

31. A device for closing a hole in a wall of a cardiovascular structure, comprising:
an endo-cameral occlusion member configured to seal against an inner surface of a wall of a cardiovascular structure around a hole in the wall, the occlusion member comprising a resiliently deformable material and configured to be radially compressed to a delivery configuration for transcatheter delivery to within the cardiovascular structure adjacent the hole and configured to radially self-expand to a deployment configuration when released from within a delivery sheath; and
an extra-cameral member coupled to the occlusion member and configured to engage an outer surface of the wall in a deployed configuration to secure the device to the wall, the extra-cameral member coupled to the occlusion member, the extra-cameral member configured to contact the outer surface of the wall when deployed, wherein the extra-cameral member comprises openings configured to receive a retaining element that retains the extra-cameral member in a radially compressed delivery configuration, wherein the extra-cameral member comprises a resiliently deformable material and is configured to be held in the radially compressed delivery configuration during transcatheter delivery and during deployment of the endo-cameral occlusion member, wherein the extra-cameral member comprises a mesh material, and wherein the extra-cameral member is configured to resiliently self-expand to a disk-shaped deployment configuration after the endo-cameral occlusion member has self-expanded to its deployment configuration when the retaining element is removed from within the openings in the extra-cameral member.

32. The device of claim 31, wherein the retaining element is a guidewire of a transcatheter delivery device, and the guidewire is removed from within the openings in the extra-cameral member by proximal withdrawal of the guidewire.

33. The device of claim 31, wherein the openings are located in an outer engagement perimeter of the extra-cameral member.

34. The device of claim 31, wherein the extra-cameral member is longitudinally elongated extending away from the occlusion member in the delivery configuration.

35. The device of claim 31, wherein the extra-cameral member expands radially outwardly and contracts longitudinally back toward the occlusion member when released from the retaining element.

* * * * *